(12) United States Patent
Kitayama et al.

(10) Patent No.: US 7,355,071 B2
(45) Date of Patent: Apr. 8, 2008

(54) METHOD FOR PREPARING 2,6-NAPHTHALENE DICARBOXYLIC ACID

(75) Inventors: Masaya Kitayama, Takarazuka (JP); Hiroyuki Wakamori, Sannan-cho (JP)

(73) Assignee: Kabushiki Kaisha Ueno Seiyaku Oyo Kenkyujo, Osaka (JP)

( * ) Notice: Subject to any disclaimer, the term of this patent is extended or adjusted under 35 U.S.C. 154(b) by 196 days.

(21) Appl. No.: 11/090,054

(22) Filed: Mar. 28, 2005

(65) Prior Publication Data

US 2005/0240056 A1    Oct. 27, 2005

(30) Foreign Application Priority Data

Mar. 26, 2004  (JP) ............... 2004-092491
Mar. 26, 2004  (JP) ............... 2004-092501
Mar. 26, 2004  (JP) ............... 2004-092510

(51) Int. Cl.
      *C07C 51/42*    (2006.01)
(52) U.S. Cl. .................................. 562/485
(58) Field of Classification Search ............... 562/483, 562/480, 485, 488, 490
      See application file for complete search history.

(56) References Cited

U.S. PATENT DOCUMENTS

| | | | |
|---|---|---|---|
| 5,149,867 A * | 9/1992 | Chen et al. ................. | 562/486 |
| 5,292,934 A * | 3/1994 | Sikkenga et al. ........... | 562/413 |
| 5,563,294 A * | 10/1996 | Holzhauer et al. ......... | 562/483 |
| 5,629,446 A * | 5/1997 | Holzhauer et al. ......... | 562/483 |
| 6,162,948 A * | 12/2000 | Iwasaki et al. ............. | 562/486 |
| 6,452,047 B1 * | 9/2002 | Shigematsu et al. ........ | 562/486 |
| 2005/0240056 A1 * | 10/2005 | Kitayama et al. ........... | 562/483 |

FOREIGN PATENT DOCUMENTS

| | | |
|---|---|---|
| GB | 1 227 144 | 4/1971 |
| JP | 62-45555 A | 2/1987 |
| JP | 3-240750 A | 10/1991 |
| JP | 6-256256 A | 9/1994 |
| WO | WO 95/10499 A1 | 4/1995 |

OTHER PUBLICATIONS

DATABASE WPI Week 199149, Derwent Publications Ltd., London, GB; AN 1991-358416, XP002444692.
DATABASE WPI Week 198714, Derwent Publications Ltd., London, GB; AN 1987-097741, XP002444693.

* cited by examiner

*Primary Examiner*—Yvonne Eyler
*Assistant Examiner*—M Louisa Lao
(74) *Attorney, Agent, or Firm*—Sughrue Mion, PLLC

(57) ABSTRACT

Disclosed is an improved method for preparing 2,6-naphthalene dicarboxylic acid from di-lower alkyl 2,6-naphthalene dicarboxylate, which is characterized in that hydrolyzing di-lower alkyl 2,6-naphthalene dicarboxylate in a specified amount of water in the presence of specified amount of hydrophobic organic solvent and an additive; that hydrolyzing di-lower alkyl 2,6-naphthalene dicarboxylate in a specific amount of a mixed solvent of non-water miscible alcohol and water; or in that di-lower alkyl 2,6-naphthalene dicarboxylate is hydrolyzed in two steps wherein the 1st step comprises hydrolyzing said ester in a water miscible organic solvent in the presence of a small amount of water, and the 2nd step comprises further hydrolyzing the reaction.

17 Claims, No Drawings

METHOD FOR PREPARING 2,6-NAPHTHALENE DICARBOXYLIC ACID

BACKGROUND OF THE INVENTION

1. Field of the Invention

The present invention relates to an improved method for preparing 2,6-naphthalenedicarboxylic acid. In particular, an improvement is provided in the method for preparing 2,6-naphthalene dicarboxylic acid, which comprises the steps of; hydrolyzing di-lower alkyl 2,6-naphthalene dicarboxylate under the presence of a basic compound to give a solution of the di-basic compound salt of 2,6-naphthalene dicarboxylic acid, and aciding out the solution to give 2,6-naphthalene dicarboxylic acid.

2. Art Related 2,6-Naphthalenedicarboxylic acid (hereinafter, abbreviated as 2,6-NDA) is useful as a monomer for manufacturing a variety of polymers such as polyethylene naphthalates, liquid crystalline polyesters or polyamides. Di-lower alkyl 2,6-naphthalenedicarboxylate (hereinafter, abbreviated as 2,6-NDC) is also useful as a monomer for manufacturing a variety of polymers. Among 2,6-NDCs, dimethyl 2,6-naphthalenedicarboxylate has preferable properties such as melting point and the like, is widely employed for the preparation of high performance polymeric materials and is considered to be most important 2,6-NDC.

A conventional method for preparing 2,6-NDA includes the step of oxidizing naphthalene derivative having alkyl and/or acyl groups at their 2 and 6 positions with molecular oxygen in the presence of a heavy metal catalyst such as cobalt or manganese. Thus obtained crude 2,6-NDA, however, comprises impurities such as aldehyde intermediates and oxidized polymer, and therefore, must be purified before being employed in manufacturing polymers. Various methods for purifying the crude 2,6-NDA have been proposed.

Among the known methods for purifying crude 2,6-NDA, a method comprising the steps of estrifying the crude 2,6-NDA with a lower alcohol such as methanol to give crude 2,6-NDC, purifying the crude 2,6-NDC by means of distillation or re-crystallization, and hydrolyzing the ester group of the purified 2,6-NDC to give purified 2,6-NDA. In said method, the step of hydrolyzing ester group is proposed to be carried out with acid catalyst or base catalyst, or by means of water under a specific condition.

In a known method for hydrolyzing ester group with acid catalyst, the ester group of 2,6-NDC is hydrolyzed in the presence of acid catalyst and an aliphatic carboxylic acid to give highly pure 2,6-NDA (Japanese Patent Application Laid Open No. 6-256256, the contents of which is herein incorporated by reference). However, this method has some problems such as long processing time and production of aliphatic carboxylate esters during the ester hydrolyzing step.

A process for preparing purified 2,6-NDA which comprises hydrolyzing a 2,6-NDC with water at a reaction temperature of at least about 450° F. or 232° C. under liquid phase condition, the amount of water present being sufficient to solubilize, at the reaction temperature, at least about 10% of the 2,6-NDA formed is proposed (U.S. Pat. No. 5,563,294, the contents of which is herein incorporated by reference). Because of the high temperature as high as 232° C. and high pressure required due to the high temperature, this method is not suitable for industrial use.

In a known method for hydrolyzing the ester group of 2,6-NDC with a basic catalyst, the ester group is hydrolyzed in water or a mixed solvent consisting of water and water miscible organic solvent with the basic catalyst, and the reaction mixture is acid precipitated to harvest the 2,6-NDA (Japanese Patent Application Laid Open No. 03-240750, the contents of which is herein incorporated by reference). However, due to the very low solubility of 2,6-NDC to water or the mixed solvent, this method has problems that the 2,6-NDC cannot be hydrolyzed completely or the hydrolyzing step takes quite a long time.

SUMMARY OF THE INVENTION

An object of the present invention is to provide a method for preparing 2,6-NDA with high purity in a short time and can be carried out under mild condition using simple equipments.

In one aspect of the present invention, an improvement in the method for preparing 2,6-NDA which comprises the steps of, hydrolyzing 2,6-NDC under the presence of a basic compound to give a solution of the di-basic compound salt of 2,6-NDA, and aciding out the dicarboxylic salt of 2,6-NDA to give 2,6-NDA is provided.

In another aspect of the present invention, a novel method for preparing 2,6-NDA which comprises the steps of, hydrolyzing 2,6-NDC under the presence of a basic compound to give a solution of the di-basic compound salt of 2,6-NDA, and aciding out the dicarboxylic salt of 2,6-NDA to give 2,6-NDA, wherein said method has characteristics in the hydrolyzing step.

In the 1st embodiment of the present invention, a method for preparing 2,6-naphthalene dicarboxylic acid, which comprises the steps of, hydrolyzing 2,6-NDC under the presence of a basic compound to give a solution of the di-basic compound salt of 2,6-NDA, and aciding out the solution to give 2,6-NDA, wherein the hydrolyzing step comprises;

hydrolyzing one part by weight of 2,6-NDC in 3-50 parts by weight of water in the presence of (A), (B) and the basic compound:

(A) 20-200 parts by weight of a hydrophobic organic solvent selected from the group consisting of an aromatic compound, a ketone and an ether per 100 parts by weight of 2,6-NDC, (B) 0.01-10 parts by weight of an additive selected from the group consisting of a polyalkylene glycol and a surface active agent per 100 parts by weight of 2,6-NDC; and separating the reaction mixture into organic phase and aqueous phase to give aqueous solution of the di-basic compound salt of 2,6-NDA is provided.

In the 2nd embodiment of the present invention, a method for preparing 2,6-naphthalene dicarboxylic acid which comprises the steps of, hydrolyzing 2,6-NDC under the presence of a basic compound to give a solution of the di-basic compound salt of 2,6-NDA, and aciding out the solution to give 2,6-NDA, wherein the hydrolyzing step comprises;

hydrolyzing one part of 2,6-NDC in 3-20 parts by weight of a mixed solvent of 10/100 to 200/100 (w/w) non-water-miscible alcohol/water in the presence of the basic compound, and separating the reaction mixture into the organic phase and aqueous phase to give an aqueous solution of the di-basic compound salt of 2,6-NDA is provided.

In the 3rd embodiment of the present invention, a method for preparing 2,6-naphthalene dicarboxylic acid which comprises the steps of, hydrolyzing 2,6-NDC under the presence of a basic compound to give a solution of the di-basic compound salt of 2,6-NDA, and aciding out the solution to give 2,6-NDA, wherein the hydrolyzing step comprises;

(1) 1st hydrolyzing step wherein one part by weight of 2,6-NDC is reacted with the basic compound in 5-20 parts by weight of a water miscible organic solvent in the presence of water in an amount of 2-10 molar times 2,6-NDC until 80% or more 2,6-NDC is converted; and (2) 2nd hydrolyzing step wherein 5-20 parts by weight of water is added to the mixture obtained by the 1st hydrolyzing step and the further reacted to give a solution of the di-basic compound salt of 2,6-NDA is provided.

In the present specification and claims, the term "lower" represents a group or moiety having 1-6 carbon atoms.

In the present specification and claims "aciding out" or "acid precipitation" represents a step to precipitate 2,6-NDA from solution of the di-basic compound salt of 2,6-NDA by adding acid to the solution.

DETAILED DESCRIPTION OF THE PREFERRED EMBODIMENTS

According to the present invention, the starting material, 2,6-NDC may be those obtained by any known method. For example, 2,6-NDC may be obtained by oxidizing naphthalene derivative having alkyl and/or acyl groups at their 2 and 6 positions with molecular oxygen in the presence of heavy metal catalyst such as cobalt or manganese to give crude 2,6-NDA, and estrifying thus obtained crude 2,6-NDA with lower alcohol in the presence of acid catalyst such as sulfuric acid or p-toluenesulfonic acid. In the present specification and claims, "lower alkyl" moiety of "di-lower alkyl 2,6-naphthalene dicarboxylate" or "2,6-NDC" may be any of straight or branched hydrocarbon groups having 1-6 carbon atoms. Among derivatives, dimethyl 2,6-naphthalenedicarboxylate is easy to available and therefore, preferably used.

According to the present invention, the basic compound used in the hydrolyzing step may preferably be alkaline metal compound. Examples of alkaline metal compounds may include alkaline metal hydroxides such as sodium hydroxide and potassium hydroxide and alkaline metal hydrogen carbonate such as sodium hydrogen carbonate and potassium hydrogen carbonate, and alkaline metal lower alkoxides such as sodium methoxide and potassium methoxide. According to the present invention, the basic compound may be added as solid compound or may be added as a solution in water or the solvent used in the hydrolyzing step. In the present specification and claims, the "di-basic compound salt of 2,6-NDA" represents a salt of 2,6-NDA wherein both carboxyl groups form salt of the basic compound.

According to the present invention, the amount of the basic compound used in the hydrolyzing step may be 1.0-5.0 equivalents, preferably 1.1-2.0 equivalents per 1 equivalent of 2,6-NDC(based on the ester group).

In the 1st embodiment of the present invention, the hydrolyzing step of 2,6-NDC is carried out in 3-50 parts by weight, preferably 5-20 parts by weight and especially 7-10 parts by weight of water per one part by weight of 2,6-NDC.

In this embodiment, the hydrolyzing step is carried out in the presence of:

(A) 20-200 parts by weight of a hydrophobic organic solvent selecting from the group consisting of an aromatic compound, a ketone and an ether per 100 parts by weight of 2,6-NDC, and (B) 0.01-10 parts by weight of an additive selected from the group consisting of a polyalkylene glycol and a surface active agent.

According to the present invention, examples of the hydrophobic organic solvent used in the 1st embodiment may include aromatic compounds such as benzene, toluene, xylene, mesitylene, ethylbenzene, nitrobenzene, chlorobenzene and dichlorobenzene; ketones such as methyl ethyl ketone, methyl isobutyl ketone and cyclohexanone; and ethers such as diethyl ether, di-n-propyl ether and d-n-butyl ether.

Among them, aromatic compounds such as benzene, toluene, xylene, mesitylene, ethylbenzene, nitrobenzene, chlorobenzene and dichlorobenzene are preferable because of their very low solubility in water.

According to the 1st embodiment of the present invention, the hydrophobic organic solvent (A) is added to the reaction in an amount of 20-200 parts by weight, preferably 100-150 parts by weight per 100 parts by weight of 2,6-NDC. In case the amount of the solvent (A) is less than 20 parts by weight, the hydrolyzing process may take longer time and the object of the present invention cannot be attained. Although this embodiment can be carried out with more than 200 parts by weight of solvent (A), too much solvent (A) is not preferable in terms of usability of the reaction vessel.

According to the 1st embodiment of the invention, the additive (B) is selected from the group consisting of a polyalkylene glycol and a surface active agent.

Polyalkylene glycol used in this embodiment is that represented by formula [I]:

$$HO-((CH_2)_n-O-)_m-H \qquad [I]$$

wherein n represents an integer of 1-6, m represents an integer equal to or more than 2.

Examples of polyalkylene glycols may include polyethylene glycol, polypropylene glycol and polyoxytetramethylene glycol. Preferably, those polyalkylene glycols are those having average molecular weight of 200-4000.

Surface active agent used in this embodiment is not specifically limited and examples may include anionic surfactant such as alkane sulfonate, linear alkylbenzene sulfonate, branched alkylbenzene sulfonate, alkylnaphthalene sulfonate, naphthalene sulfonate formaldehyde condensate, alkyl sulfonate, polyoxyethylene alkylether phosphate and fatty acid monocarboxylate, nonionic surfactant such as glycerol fatty acid ester, sorbitan fatty acid ester, polyoxyethylene alkyl ether, polyoxyethylene alkylphenyl ether, polyethylene glycol fatty acid ester and polyoxyethylene sorbitan fatty acid ester, cationic surfactants such as alkyl amine salt and quaternary ammonium salt; and amphoteric surfactants such as alkyl betaine. Among them, polyalkylene glycol, especially polyethylene glycol is preferably used as additive (B) in this embodiment in terms reduced environmental burden and chemical stability.

The amount of additive (B) used in this embodiment per 100 parts by weight of 2,6-NDC is 0.01-10 parts by weight and preferably, 0.1-5 parts by weight.

According to the 1st embodiment, the hydrolyzing step may be carried out at 60-100° C. and preferably at 70-90° C. In case the employed reaction temperature is higher than the boiling point of the reaction system, the reaction may be carried out under pressure using a pressure resistant sealed reaction vessel.

The hydrolyzing reaction may be continued until almost all 2,6-NDC is converted into the di-basic compound salt of 2,6-NDA and preferably, the reaction time is 1-5 hours.

After the reaction is completed, the reaction mixture is stood still to separate the same into organic and aqueous phases. In order to avoid precipitation of salt of 2,6-NDA at this stage, this separation process is preferably carried out under heating at 40-80° C.

In the 1st embodiment, the separated organic phase may be used in the hydrolyzing step again as such. If desired, the organic phase is purified by distillation or washing with water before use.

The separated aqueous phase may be filtered to remove insoluble impurities or treated with absorbent such as activated carbon to remove colorant or metal impurities before being subjected to the aciding out step. The aqueous phase contains the di-basic compound salt of 2,6-NDA dissolved therein and therefore, 2,6-NDA can be obtained by aciding out, i.e. by adding an acid to the solution.

According to the present invention, acids used in the aciding out step are not limited and mineral acids are preferably used. Examples of mineral acids may include binary acids such as hydrochloric acid and hydrofluoric acid, oxo acids such as sulfuric acid, nitric acid, phosphoric acid and perchloric acid.

2,6-NDA may be isolated from the slurry of 2,6-NDA obtained by the aciding out step in a conventional manner such as centrifugation or filtration with filter press. If desired, the isolated 2,6-NDA may be washed with cold water and warm water, and dried to give purified 2,6-NDA.

According to the 2nd embodiment of the present invention, the hydrolyzing step comprises the steps of;

hydrolyzing one part of 2,6-NDC in 3-20 parts by weight of a mixed solvent of 10/100 to 200/100 (w/w) non-water-miscible alcohol/water in the presence of the basic compound, and separating the reaction mixture into the organic phase and aqueous phases to give an aqueous solution of the di-basic compound salt of 2,6-NDA.

In the 2nd embodiment, the non-water-miscible alcohol may be any of those being separated into aqueous phase and organic phase when mixed with water under the room temperature. Preferable non-water miscible alcohols may be selected from the group consisting of n-butanol, 2-ethylhexyl alcohol, 2-phenoxyethanol, benzyl alcohol and a mixture thereof.

The weight ratio of non-water miscible alcohol to water in the mixed solvent used in this embodiment is 10/100-200/100, and preferably, 13/100-100/100. In case the basic compound is added to the reaction as solution in water or non-water miscible alcohol, the weight ratio in the reaction mixture after the basic compound is added should be in the above limited range.

The amount of the mixed solvent may be 3-20 parts by weight and preferably, 5-10 parts by weight per one part by weight of 2,6-NDC. When the amount of the mixed solvent is less than 3 parts by weight, the concentration of the substrate in the reaction mixture becomes too high and it becomes harder to stir well the mixture. Consequently, the reaction speed becomes very slow. When the amount of the mixed solvent is more than 20 parts by weight, the amount of the di-basic compound salt of 2,6-NDA contained in the organic phase upon separation increases. Consequently, the final yield will be decreased.

In this embodiment, the hydrolyzing step may be carried out at 40-100° C. and preferably at 60-100° C. In case the employed reaction temperature is higher than the boiling point of the reaction system, the reaction may be carried out under pressure using a pressure resistant sealed reaction vessel.

The hydrolyzing reaction may be continued until almost all 2,6-NDC is converted into the di-basic compound salt of 2,6-NDA and preferably, the reaction time is 1-5 hours.

After the reaction is completed, the reaction mixture is stood still and separated into the organic and aqueous phases. In order to avoid precipitation of salt of 2,6-NDA at this stage, this separation process is preferably carried out under heating at 40-80° C.

The separated organic phase may be used in the hydrolyzing step again as such. If desired, the organic phase is purified by purification process such as distillation before being used again.

The separated aqueous phase may be filtered to remove insoluble impurities or treated with absorbent such as activated carbon to remove colorant or metal impurities before being subjected to the aciding out step. The aqueous phase contains carboxylic acid salt dissolved therein and therefore, 2,6-NDA can be obtained by aciding out, i.e. adding an acid to the aqueous solution In the 2nd embodiment, the aciding out step may be carried out in the same manner as the 1st embodiment so that purified 2,6-NDA is obtained.

In the 3rd embodiment of the present invention, the hydrolyzing step comprises 1st and 2nd hydrolyzing steps. In the 1st hydrolyzing step, 2,6-NDC is hydrolyzed in a water miscible organic solvent in the presence of small amount water. The amount of water present in the reaction mixture of the 1st hydrolyzing step of this embodiment is 2-10 mole, preferably 4-6 mole per 1 mole of 2,6-NDC.

In the specification and claims, "water miscible organic solvent" means an organic solvent which is freely miscible with water. Examples of the water miscible organic solvents may include alcohols such as methanol, ethanol, isopropanol, 2-methoxyethanol, 2-ethoxyethanol, ethyleneglycol, glycerine and polyethylene glycol 200; ketones such as acetone; aprotic polar solvent such as N,N-dimethylacetamide, N,N-dimethylformamide, dimethyl sulfoxide, hexamethyl phosphoramide and N-methyl-2-pyrrolidone. Those water miscible organic solvent may be used solely or in combination of two or more. Among the above, alcohol is preferable.

In the 1st hydrolyzing step, the amount of the water miscible organic solvent may be 5-20 parts by weight, preferably, 7-10 parts by weight per one part by weight of 2,6-NDC. When the amount of the water miscible organic solvent is less than 5 parts by weight, the slurry concentration of the reaction mixture becomes too high and it becomes harder to stir well the mixture. Consequently, the reaction speed will become very slow. When the amount of the water miscible organic solvent is more than 20 parts by weight, considerable amount of 2,6-NDA will remain in the liquid phase upon aciding out the solution. Consequently, the final yield will be decreased.

In the 3rd embodiment, the 1st hydrolyzing step may be carried out at 40-100° C., preferably 60-100° C. and most preferably, may be carried out at around the boiling point of the reaction system under reflux.

The 1st hydrolyzing step is carried out until at least 80% of the starting 2,6-DNC is converted. In this context, "2,6-NDC is converted" means 2,6-NDC is converted into either the corresponding mono-basic compound salt of 2,6-NDC (monoester) or corresponding di-basic compound salt of 2,6-NDA. In the 1st hydrolyzing step, the method of confirming the amount of converted 2,6-NDC is not specifically limited and high speed liquid chromatography, for example, may be used.

According to this embodiment, at least 80%, preferably at least 90% and more preferably at least 95% of 2,6-NDC is converted in the 1st hydrolyzing step. The reaction time of the 1st hydrolyzing step may preferably be 1-5 hours.

According to the 3rd embodiment of the invention, water is added to the reaction mixture obtained by the 1st hydrolyzing step. The amount of water to be added upon the 2nd hydrolyzing step is 5-20 parts by weight, preferably 7-10 parts by weight per one part by weight of the starting amount of 2,6-NDC. When the amount is less than 5 parts by weight, salt of 2,6-NDA monoester tends to precipitate and the reaction speed tends to slow down. When the amount is more than 20 parts by weight, the volume efficiency of the usability of the reaction vessel may become less efficient.

The 2nd hydrolyzing step may be carried out under the temperature same as that of the 1st hydrolyzing step. The preferable reaction time for the 2nd hydrolyzing step may be 0.5-2 hours.

The reaction mixture obtained by the 2nd hydrolyzing step may be filtrated to remove insoluble impurities or treated with absorbent such as activated carbon to remove colorant or metal impurities before being subjected to the aciding out step. The reaction mixture obtained by the 2nd hydrolyzing step comprises di-basic compound salt of 2,6-NDA dissolved therein and therefore, 2,6-NDA can be obtained by aciding out, i.e. by adding an acid to the solution.

In order to avoid contamination of 2,6-NDA with the salt precipitated by the aciding out procedure, the same amount of water that added upon the 2nd hydrolyzing step may be added to the reaction mixture before the aciding out step.

According to the 3rd embodiment, the aciding out process may be carried out in the same manner as that of the 1st embodiment.

According to the present invention, the obtained 2,6-NDA by any of the embodiments 1-3 may preferably used as a monomer for manufacturing various polymers such as polyethylene naphthalates, liquid crystalline polyesters and polyamides.

The present invention will be further illustrated by the examples shown below:

EXAMPLE 1

Dimethyl 2,6-naphthalene dicarboxylate 60 g (0.245 mole), water 600 g, xylene 120 g and polyethylene glycol #4000 (average molecular weight: 3000, reagent grade, Wako Pure Chemical Industries, Ltd., Osaka, Japan) 1.2 g and 48% aqueous sodium hydroxide 43.0 g (0.52 mole) were charged in a 1L four-neck glass flask equipped with stirrer, thermometer and Dimroth condenser.

The mixture was heated with stirring from the room temperature to 90° C. over 30 minutes, and reacted under reflux for 3 hours. After the reaction was completed, the mixture was cooled to 60° C., stood at the temperature and separated into the organic and aqueous phases.

The obtained aqueous phase was added with 30% aqueous sulfuric acid 93.6 g (0.283 mole) and the precipitated 2,6-NDA was collected by suction filtration. Thus obtained 2,6-NDA was dispersed in warm water, then collected by suction filtration, and dried at 80° C.

The obtained 2,6-NDA was 52.9 g (0.244 mole) and yield based on the starting dimethyl 2,6-naphthalene dicarboxylate was 99.5%. That is, 2,6-NDA was obtained from 2,6-NDC in a quantitative manner.

EXAMPLES 2-8 AND COMPARATIVE EXAMPLES 1 AND 2

2,6-NDA was prepared from dimethyl 2,6-naphthalene dicarboxylate in the same manner as Example 1 under the conditions shown in Table 1.

The hydrophobic organic solvent and additives used in the table are as follows:

Hydrophobic Organic Solvents
  A: Toluene, B: Xylene, C: Cyclohexanone

Additives:
  a: Polyethylene glycol #4000, average molecular weight: 3000, reagent grade (Wako Pure Chemical Industries, Ltd., Osaka, Japan)
  b: Dishwashing detergent, comprising 27% surfactant [linear alkylbenzene surfactant and sodium alkyl ether sulfate] (Lion Corporation, Tokyo, Japan)
  c: Dishwashing detergent, comprising 24% surfactant [polyoxyethylene alkylether, fatty acid alkanol amide and sodium alkyl ether sulfate] (Lion Corporation, Tokyo, Japan)
  d: Dishwashing detergent, comprising 20% surfactant [sodium alkyl ether sulfate, sodium alpha olefin sulfonate, fatty acid alkanol amide] (Lion Corporation, Tokyo, Japan)
  e: Dishwashing detergent, comprising 19% surfactant [sodium alkyl ether sulfate] (Kao Corporation, Tokyo, Japan)
  f: Dishwashing detergent, comprising 18% surfactant [polyoxyethylene alkyl ether] (Kao Corporation, Tokyo, Japan)

TABLE 1

|  | hydrophobic organic solvent | additive | reaction temp. | reaction time | 2,6-NDA yield |
|---|---|---|---|---|---|
| Ex. 2 | A | a | 80° C. | 3 Hr. | >99% |
| Ex. 3 | C | a | 95° C. | 3 Hr. | >99% |
| Ex. 4 | B | b | 90° C. | 3 Hr. | >99% |
| Ex. 5 | B | c | 90° C. | 3 Hr. | >99% |
| Ex. 6 | B | d | 90° C. | 3 Hr. | >99% |
| Ex. 7 | B | e | 90° C. | 3 Hr. | >99% |
| Ex. 8 | B | f | 90° C. | 4 Hr. | >99% |
| Com. Ex. 1 | B | none | 90° C. | 5 Hr. | * |
| Com. Ex. 2 | none | a | 100° C. | 5 Hr. | * |

* The reaction mixture was not completely hydrolyzed and 2,6-NDA was not isolated.

EXAMPLE 9

Dimethyl 2,6-naphthalene dicarboxylate 50 g (0.204 mole), mixed solvent consisting of n-butanol 40 g and water 260 g (16/100 w/w) and 48% aqueous sodium hydroxide 35.8 g (0.43 mole) were charged in a 1L four-neck glass flask equipped with stirrer, thermometer and Dimroth condenser. The weight ratio of n-butanol/water in the reaction mixture was 15/100.

The mixture was heated with stirring from the room temperature to 80-85° C. over 30 minutes, and reacted under reflux for 30 minutes. After the reaction was completed, the mixture was cooled to 60° C., stood at the temperature and separated into the organic and aqueous phases.

The obtained aqueous phase was added with 30% aqueous sulfuric acid 78 g (0.236 mole) and the precipitated 2,6-NDA was collected by suction filtration. Thus obtained 2,6-NDA was dispersed in warm water, then collected by suction filtration, and dried at 80° C.

The obtained 2,6-NDA was 43.9 g (0.203 mole), that is, 2,6-NDA was obtained in short time from 2,6-NDC in a quantitative manner.

EXAMPLE 10

The same reaction of example 9 except for using the organic phase 50 g which was separated from the reaction mixture in the example 9 was used in stead of n-butanol. The organic phase contained about 23% of water. Accordingly, the weight ratio of n-butanol/water in the reaction mixture of this example was 14/100. The obtained 2,6-NDA was 44.0 g (0.203 mole). It was confirmed that the organic phase separated from the reaction mixture in this method can be used again as non-miscible alcohol.

EXAMPLE 11

Dimethyl 2,6-naphthalene dicarboxylate 40 g (0.163 mole), mixed solvent consisting of n-butanol 200 g and water 300 g (67/100 w/w) and 48% aqueous sodium hydroxide 28.6 g (0.34 mole) were charged in the 1L four-neck glass flask equipped with stirrer, thermometer and Dimroth condenser. The weight ratio of n-butanol/water in the reaction mixture was 63.5/100.

The mixture was heated with stirring from the room temperature to 80-85° C. over 30 minutes, and reacted under reflux for 30 minutes. After the reaction was completed, the mixture was cooled to 60° C., stood at the temperature and separated into the organic and aqueous phases.

The obtained aqueous phase was added with 30% aqueous sulfuric acid 62.4 g (0.189 mole) and the precipitated 2,6-NDA was collected by suction filtration. Thus obtained 2,6-NDA was dispersed in warm water, then collected by suction filtration, and dried at 80° C.

The obtained 2,6-NDA was 34.9 g (0.161 mole), that is, 2,6-NDA was obtained from 2,6-NDC in short time in a quantitative manner.

COMPARATIVE EXAMPLE 3

The reaction of example 9 was carried out except for water 300 g was used instead of the mixed solvent and the reaction was carried out at 100° C., i.e. heated to 100° C. over 30 minutes and reacted at the temperature for 30 minutes. In this comparative example, 2,6-NDC was hardly hydrolyzed in this example.

COMPARATIVE EXAMPLE 4

The reaction of example 9 was carried out except for n-butanol 300 g was used instead of the mixed solvent and the reaction mixture was heated to 100° C. over 30 minutes and reacted at the temperature for 5 hours. In this comparative example, 2,6-NDC was not completely hydrolyzed.

EXAMPLE 12

Dimethyl 2,6-naphthalene dicarboxylate 40 g (0.164 mole), methanol 400 g and 48% aqueous sodium hydroxide 28.6 g (0.34 mole) were charged in a 1L four-neck glass flask equipped with stirrer, thermometer and Dimroth condenser. The water content in this reaction mixture was 5 molar times of the dimethyl 2,6-naphthalene dicarboxylate.

The mixture was heated with stirring to 65° C. and reacted at the temperature (1st hydrolyzing step). After 1.5 hours, small amount of the reaction mixture was analyzed by means of high speed liquid chromatograph and confirmed that approximately 100% of the starting dimethyl 2,6-naphthalene dicarboxylate was converted into sodium mono salt of 2,6-NDA mono methyl ester or disodium salt of 2,6-NDA, and at the time, the 1st hydrolyzing reaction was stopped.

Water 400 g was added to the obtained reaction mixture and the resulting mixture was heated to 74° C. and further reacted for 30 minutes at the temperature (2nd hydrolyzing step). After the reaction was completed, water 400 g was added and thus obtained solution was heated to 80° C. At the temperature, 30% aqueous sulfuric acid 62 g was added to the solution drop wise over 30 minutes to give slurry of 2,6-NDA.

The precipitated 2,6-NDA was collected by suction filtration. Thus obtained 2,6-NDA was dispersed in warm water, then collected by suction filtration, and dried at 80° C. to give crystalline 2,6-NDA 35.4 g (0.164 mole, yield >99%), that is, 2,6-NDA was obtained from 2,6-NDC in a quantitative manner.

EXAMPLES 13-18

2,6-NDA was prepared from dimethyl 2,6-naphthalene dicarboxylate in the same manner as Example 12 under the conditions shown in Table 2. In each examples, small amount of the reaction mixture of the 1st hydrolyzing reaction was obtained after 1.5 hours of reaction and it was confirmed that approximately 100% of 2,6-NDC was converted into mono sodium salt of 2,6-NDA monomethyl ester or disodium salt of 2,6-NDA at the time.

TABLE 2

| | water miscible organic solvent | Reaction Temp.(° C.) | | obtained 2,6-NDA (yield) |
|---|---|---|---|---|
| | | 1st | 2nd | |
| Ex. 13 | acetone | 55 | 65 | 35.2 g (>99%) |
| Ex. 14 | isopropanol | 80 | 81 | 35.1 g (>99%) |
| Ex. 15 | 2-methoxyethanol | 90 | 100 | 35.2 g (>99%) |
| Ex. 16 | polyethylene glycol 200 | 90 | 100 | 35.1 g (>99%) |
| Ex. 17 | glycerin | 90 | 100 | 35.1 g (>99%) |
| Ex. 18 | hexamethyl phosphoramide | 90 | 100 | 35.2 g (>99%) |

COMPARATIVE EXAMPLE 5

Dimethyl 2,6-naphthalene dicarboxylate 40 g (0.164 mole), 50% aqueous methanol 800 g and 48% aqueous sodium hydroxide 28.6 g (0.34 mole) were charged in a 2 L four-neck glass flask equipped with stirrer, thermometer and Dimroth condenser.

The mixture was heated with stirring to 90° C. and reacted at the temperature under reflux for 5 hours. After 5 hours, small amount of the reaction mixture was analyzed by means of high speed liquid chromatograph and found that the reaction mixture comprised about 40wt % of dimethyl 2,6-naphthalene dicarboxylate, about 40wt % of mono sodium salt of 2,6-naphthalene dicarboxylic acid mono methyl ester and about 20% of disodium salt of 2,6-naphthalene dicarboxylic acid. That is, 5 hours reaction was not enough to proceed the hydrolyzing reaction completely.

What is claimed is:

1. A method for preparing 2,6-naphthalene dicarboxylic acid, which comprises the steps of, hydrolyzing di-lower alkyl 2,6-naphthalene dicarboxylate under the presence of a basic compound to give a solution of the di-basic compound salt of 2,6-naphthalene dicarboxylic acid, and aciding out the solution to give 2,6-naphthalene dicarboxylic acid, wherein the hydrolyzing step comprises;

hydrolyzing one part by weight of di-lower alkyl 2,6-naphthalene dicarboxylate in 3-50 parts by weight of water in the presence of (A), (B) and the basic compound:

(A) 20-200 parts by weight of a hydrophobic organic solvent selected from the group consisting of an aromatic compound, a ketone and an ether per 100 parts by weight of di-lower alkyl 2,6-naphthalene dicarboxylate, (B) 0.01-10 parts by weight of an additive selected from the group consisting of a polyalkylene glycol and a surface active agent per 100 parts by weight of di-lower alkyl 2,6-naphthalene dicarboxylate; and separating the reaction mixture into organic phase and aqueous phase to give the aqueous solution of the di-basic compound salt of 2,6-naphthalene dicarboxylic acid.

2. The method of claim 1, wherein the hydrophobic organic solvent is at least one selected from the group consisting of benzene, toluene, xylene, mesitylene, ethylbenzene, nitrobenzene, chlorobenzene and dichlorobenzene.

3. The method of claim 1, wherein the additive (B) is polyalkylene glycol.

4. The method of claim 3, wherein the polyalkylene glycol is polyethylene glycol.

5. The method of claim 1, wherein the organic phase obtained after the hydrolyzing step is used again as the hydrophobic organic solvent in the hydrolyzing step.

6. The method of claim 1, wherein the basic compound is selected from the group consisting of an alkaline metal hydroxide, an alkaline metal carbonate, an alkaline metal bicarbonate and an alkaline metal lower alkoxide.

7. The method of claim 1, wherein the amount of the basic compound used in the hydrolyzing step is 1.0-5.0 equivalent per 1 equivalent of di-lower alkyl 2,6-naphthalene dicarboxylate (based on the ester group).

8. A method for preparing 2,6-naphthalene dicarboxylic acid which comprises the steps of, hydrolyzing di-lower alkyl 2,6-naphthalene dicarboxylate under the presence of a basic compound to give a solution of the di-basic compound salt of 2,6-naphthalene dicarboxylic acid, and aciding out the solution to give 2,6-naphthalene dicarboxylic acid, wherein the hydrolyzing step comprises;

hydrolyzing one part by weight of di-lower alkyl 2,6-naphthalene dicarboxylate in 3-20 parts by weight of a mixed solvent of 10/100 to 200/100 (w/w) non-water-miscible alcohol/water in the presence of the basic compound, and separating the reaction mixture into the organic phase and aqueous phase to give the aqueous solution of the di-basic compound salt of 2,6-naphthalene dicarboxylic acid.

9. The method of claim 8, wherein the non-water miscible alcohol is at least one selected from the group consisting of n-butanol, 2-ethyihexyl alcohol, 2-phenoxyethanol and benzyl alcohol.

10. The method of claim 8, wherein the organic phase obtained after the hydrolyzing step is used again as the non-water miscible alcohol in the hydrolyzing step.

11. The method of claim 8, wherein the basic compound is selected from the group consisting of an alkaline metal hydroxide, an alkaline metal carbonate, an alkaline metal bicarbonate and an alkaline metal lower alkoxide.

12. The method of claim 8, wherein the amount of the basic compound used in the hydrolyzing step is 1.0-5.0 equivalent per 1 equivalent of di-lower alkyl 2,6-naphthalene dicarboxylate (based on the ester group).

13. A method for preparing 2,6-naphthalene dicarboxylic acid which comprises the steps of, hydrolyzing di-lower alkyl 2,6-naphthalene dicarboxylate under the presence of a basic compound to give a solution of the di-basic compound salt of 2,6-naphthalene dicarboxylic acid, and aciding out the solution to give 2,6-naphthalene dicarboxylic acid, wherein the hydrolyzing step comprises;

(1) 1st hydrolyzing step wherein one part by weight of di-lower alkyl 2,6-naphthalene dicarboxylate is reacted with the basic compound in 5-20 parts by weight of a water miscible organic solvent in the presence of water in an amount of 2-10 molar times 2,6-NDC until at least 80% of di-lower alkyl 2,6-naphthalene dicarboxylate is converted; and (2) 2nd hydrolyzing step wherein 5-20 parts by weight of water is added to the mixture obtained by the 1st hydrolyzing step and the resulting mixture is further reacted to give the solution of the di-basic compound salt of 2,6-naphthalene dicarboxylic acid.

14. The method of claim 13, wherein the water miscible organic solvent is at least one selected from the group consisting of an alcohol, a ketone and aprotic polar solvent.

15. The method of claim 13, wherein the water miscible organic solvent is at least one selected from the group consisting of methanol, ethanol, isopropanol, 2-methoxyethanol, 2-ethoxyethanol, ethyleneglycol, glycerine and polyethylene glycol 200.

16. The method of claim 13, wherein the basic compound is selected from the group consisting of an alkaline metal hydroxide, an alkaline metal carbonate, an alkaline metal bicarbonate, and an alkaline metal lower alkoxide.

17. The method of claim 13, wherein the amount of the basic compound used in the hydrolyzing step is 1.0-5.0 equivalent per 1 equivalent of di-lower alkyl 2,6-naphthalene dicarboxylate (based on the ester group).

* * * * *